United States Patent [19]
Hu et al.

[11] Patent Number: 6,037,328
[45] Date of Patent: Mar. 14, 2000

[54] METHOD AND COMPOSITION FOR REWETTING AND PREVENTING DEPOSITS ON CONTACT LENS

[75] Inventors: Zhenze Hu, Pittsford, N.Y.; Edward J. Ellis, Lynnfield, Mass.; John Denick, Jr., Pittsford, N.Y.

[73] Assignee: Bausch & Lomb Incorporated, Rochester, N.Y.

[21] Appl. No.: 09/218,505

[22] Filed: Dec. 22, 1998

[51] Int. Cl.⁷ .......................... A61K 31/70; A61K 31/08
[52] U.S. Cl. .......................................... 514/23; 514/772.3
[58] Field of Search ...................... 514/23, 772.3

[56] References Cited

U.S. PATENT DOCUMENTS

| | | | |
|---|---|---|---|
| 5,401,327 | 3/1995 | Ellis et al. | 134/42 |
| 5,773,396 | 6/1998 | Zhang et al. | 510/115 |

*Primary Examiner*—Zohreh Fay
*Attorney, Agent, or Firm*—Chris P. Konkol; Denis A. Polyn

[57] ABSTRACT

The present invention is directed to an ophthalmic solution for the treatment of contact lenses while worn in the eye. In particular, the composition contains ethoxylated glucose derivative, tyloxapol, and a polyoxyethylene-polyoxypropylene nonionic surfactant. The ophthalmic solution containing such a combination of components can be applied, in the form of drops, to the eye or to contact lens in the eye. In one embodiment of the invention, the composition is used for reducing unwanted lipid or protein deposition on extended-wear lenses, including lenses made from relatively hydrophobic materials such as silicon hydrogels.

7 Claims, No Drawings

METHOD AND COMPOSITION FOR REWETTING AND PREVENTING DEPOSITS ON CONTACT LENS

FIELD OF THE INVENTION

This invention relates to a composition and method for rewetting and preventing deposits on contact lenses. In particular, the composition is an ophthalmic solution comprising the combination of tyloxapol, an ethoxylated glucose, and a non-ionic surfactant comprising a polyoxyethylene-polyoxypropylene block polymer or adduct thereof. The composition inhibits the deposition of lipids and the like on contact lenses.

BACKGROUND OF THE INVENTION

Contact lenses in wide use today fall into two categories. First, there are the hard or rigid corneal type lenses that are formed from materials prepared by the polymerization of acrylic esters, such as polymethylmethacrylate (PMMA). Secondly, there are the gel, hydrogel or soft type of lenses made by polymerizing such monomers as 2-hydroxyethyl methacrylate (HEMA) or, in the case of extended wear lenses, made by polymerizing silicon-containing monomers or macromonomers. Solutions that wet the lenses before insertion in the eye are required for both the hard and soft types of contact lenses, although their formulations have tended to differ based on their different properties. After the contact lenses are inserted in the eye, ophthalmic solutions for rewetting, lubricating, and/or enhancing wearer comfort are sometimes applied to the eye by means of a drop dispenser.

Isotonic solutions for improving the comfort of wearing soft contact lenses by being added directly to the contact lens in the eye are known. Such solutions typically contain viscosity enhancing agents, lubricants, surfactants, buffers, preservatives, and salts. For example, U.S. Pat. No. 4,529,535 to Sherman discloses a rewetting solution that is particularly useful for rigid silicone copolymer contact lenses, including extended wear lenses. In one embodiment, the rewetting solution contains the combination of hydroxyethylcellulose, polyvinyl alcohol, and polyvinylpyrrolidone.

U.S. Pat. No. 4,786,436 to Ogunbiyi, et al. discloses a wetting solution comprising collagen and other demulcents such as hydroxylethyl cellulose, methyl cellulose, carboxymethyl cellulose, hydroxypropyl methylcellulose, hydroxylpropyl-cellulose and the like.

U.S. Pat. No. 4,748,189 to Su et al. discloses ophthalmic solutions for improving the exchange of fluid in the area outside a hydrogel contact lens in the area underneath the hydrogel contact lens, in order to permit tear exchange to occur, thereby preventing the accumulation of waste matter and debris under the lens. The solution contains a hydrogel flattening agent, for example urea, glycerin, propylene glycol, sorbitol, or an amino-ethanol. Surfactants that are useful in the solution include poloxamer and tyloxapol. Suitable lubricants include hydroxylethylcellulose, polyvinylalchol, and polyvinylpyrrolidone.

U.S. Pat. No. 5,209,865 to Winterton et al. discloses a conditioning solution for contact lenses that comprises a combination of a poloxamine and a poloxamer surfactant each having an HLB (hydrophilic-lipophilic balance) of seven or below. The solution according to the invention forms a uniform hydrophilic film on a lens surface for which proteins have very little affinity. As such, a contact lens contacted by the solution is said to have a coating that provides a prophylactic effect to the lens.

U.S. Pat. No. 5,604,189 and U.S. Pat. No. 5,773,396 to Zhang et al. disclose a composition for cleaning and wetting contact lenses comprising (i) a non-amine polyethyleneoxy-containing compound having an HLB of at least about 18, (ii) a surface active agent having cleaning activity for contact lens deposits that may have an HLB less than 18, and (iii) a wetting agent. Such compositions can include, as the wetting agent, an ethoxylated glucose derivative such as glucam, also disclosed in U.S. Pat. No. 5,401,327 to Ellis et al. Tyloxapol is a conventional surface active agent, used for example in Allergan's Complete® multipurpose solution, which agent has cleaning activity for contact-lens deposits and has an HLB less than 18.

Unlike hard lenses, the soft type of contact lenses have a tendency to bind and concentrate significantly more fluids, environmental pollutants, water impurities. Likewise, the soft type of contact lenses is more susceptible to the deposition of protein or lipids or both. Thus, the use of enzymes or equivalent protein-removing agents has been conventionally employed for weekly or daily protein removal from worn lenses. In contrast, surfactant cleaning agents in daily lens care solutions are useful for the removal of lipid or lipid-like materials from the lenses. With the advent of extended wear lenses, however, in which lenses are worn overnight and even continuously over a plurality of whole days, night and day, the lens wearers no longer have the opportunity to remove, by means of the conventional lens care solutions, the depositions that have accumulated over the day.

It would, therefore, be desirable to have a solution that could be applied to the eye that not only rewets the lens but also cleans and/or prevents the deposition of lipids until such time as the lens is removed from the eye and cleaned or disposed. However, it does not necessarily follow that cleaning agents that can be used in cleaning solutions in which contact lenses are immersed for several hours or more would be effective when applied in the form of eyedrops to a lens in the eye. In particular, cleaning agents that are designed to prevent the deposition of lipids on a lens must have an extended effect on a lens within the eye. At the same time, cleaning agents must be selected that are very safe and comfortable, especially as they would be expected to associate with the lens surfaces while in the eye.

SUMMARY OF THE INVENTION

The present invention is directed to a rewetting solution for contact lenses comprising an ethoxylated glucose derivative, tyloxapol, and a non-ionic surfactant comprising a polyoxyethylene-polyoxypropylene or adduct thereof. An ophthalmic solution containing such a combination of components can be applied in the form of drops to the contact lens while they are in the eye. Thus, a system useful to prevent the deposition of lipids as well as for rewetting or lubricating contact lenses while in the eye comprises an drop dispenser and a plastic container holding between about 1 and about 30 ml of an ophthalmic solution comprising:

(a) an effective amount of ethoxylated glucose derivative,
(b) an effective amount of tyloxapol,
(c) an effective amount of a non-ionic surfactant comprising a polyoxyethylene-polyoxypropylene polymer or adduct thereof.

Preferably, the non-ionic surfactant has a cloud point of at least 50° C., preferably above 90° C., at a concentration of one percent. In one embodiment of the invention, the solution also comprises an effective amount of a polymeric demulcent. Preferably, the polymeric demulcent is a cellulosic polymer.

Such a solution is especially advantageous for the treatment of soft lenses that are capable of use for extended wear. It is especially effective for use on silicone hydrogel lenses that potentially can be worn for seven days and even longer. Additional ingredients that may be included in a solution according to the present invention are a sequestering agent, which may be present in an amount of 0.01 to 2.0% by weight, and an effective amount of a buffering agent to maintain the pH between about 5.0 and 8.0, preferably 5.5 to 7.5.

The invention is also directed to a method of using the foregoing composition. The objects, features, and advantages of the various embodiments of the present invention will become more readily apparent from the following detailed description.

DETAILED DESCRIPTION OF THE INVENTION

The present invention is directed to an ophthalmic solution that is applied in the form of drops to a contact lens while it is worn in the eye and which is useful for rewetting or lubricating the lens as well as for prophylactically cleaning the lens by preventing the deposition of lipids or other depositions on the lens.

As indicated above, while the present invention can be used in connection with a variety of soft lenses, it is especially useful with respect to hydrophilic lenses made from polymers having repeat units derived from hydrophilic monomers such as hydroxyethyl methacrylate, polyvinylpyrrolidone, dimethylacrylamide, methacrylic acid, or the like. These include hydrogels belonging to Groups I to IV (FDA categories). Group IV is distinguished from Groups I to III by having higher water content and is distinguished from Group I and II by being more ionic. Typically, Group IV lenses have a water content greater than 50% by weight. High water content is associated with materials having high oxygen permeability, resulting in the increasing popularity of Group IV lenses, especially disposable and frequent-replacement lenses. Such materials include, but are not limited to, bufilcon A, etafilcon A, methafilcon A, ocufilcon C, perfilcon A, phemfilcon A, and vifilcon A. Materials containing methacrylic acid monomers include methafilcon B, ocufilcon D, methafilcon A, and etafilcon A (USAN and the USAP Dictionary of Drug Names). Lenses made from the foregoing materials are commercially available from a variety of sources. Such lenses include daily-wear lenses, extended-wear lenses, planned-replacement lenses, and disposable lenses.

The present invention can also be used in connection with soft lenses made from a silicone hydrogel material. Such lens materials, for example, are disclosed in U.S. Pat. No. 5,260,000 to Nandu, et al. (for example, see Formulation A). Such materials are known as balafilcon A. Lenses made from silicone hydrogel materials are more hydrophobic that other types of soft lenses and are, therefore, especially prone to lipid deposition.

As indicated above, the lens-care ophthalmic solution of the invention for preventing lipid deposition on contact lenses requires the combination of an ethoxylated glucose derivative, tyloxapol, and a non-ionic surfactant that is a polyoxyethylene-polyoxypropylene block polymer or adduct thereof. It has been found that this combination of surfactants is not only effective in preventing the deposition of lipids, but is comfortable for use in the eye. Without wishing to be bound by theory, each of the three ingredients is believed to have a unique function in the combination; the non-ionic polyoxyethylene-polyoxypropylene surfactant is believed to function to some extent as a comfort agent, perhaps masking any potential irritation of the primary cleaner, as suggested in U.S. Pat. No. 5,604,189 to Zhang et al. The tyloxapol is believed to be the primary cleaning agent in the eye. The ethoxylated glucose derivative is believed to function as a wetting agent. As such, it may remain attached to the lens and assist in the spreading of the cleaner and the comfort agent on the lens. These separate functions, however, should not be viewed as clear-cut and exclusive. For example, the non-ionic polyoxyethylene-polyoxypropylene surfactant may have some cleaning effect, but not as much as the combination with the tyloxapol. Similarly, the surfactants are not as effective and not as durable in the absence of the wetting agent. Also, the attachment of one or more of the solution components to the lens in the eye is believed to reduce the hydrophobicity of the lens surface, especially in the case of a silicon hydrogel, which may reduce the affinity of lipids to the lens surface. The surfactants may not only prevent the deposition of lipids, but also to some extent may loosen deposits on the lens; wherein removal is assisted by the natural cleaning action of blinking.

The non-ionic polyoxyethylene-polyoxypropylene surfactants employed in the present invention preferably have a cloud point of at least 50° C. at a concentration of 1 percent and more preferably also has an HLB of at least 18. Such surfactants can be selected, for example, from the group of commercially available surfactants having the name poloxamine or poloxamer, as adopted by *The CTFA International Cosmetic Ingredient Dictionary*. Poloxamine surfactants consist of a poly(oxypropylene)-poly(oxyethylene) adduct of ethylene diamine having a molecular weight from about 7,500 to about 27,000 wherein at least 40 weight percent of said adduct is poly(oxyethylene). Such surfactants are available from BASF Wyandotte Corp., Wyandotte, Mich., under the registered trademark "Tetronic". An analogous series of surfactants is the poloxamer series which is a polyoxyethylene, polyoxypropylene block polymer available from BASF Wyandotte Corp., Parsippany, N.J. 07054 under the trademark "Pluronic".

The HLB of a surfactant is known to be a major factor in determining the emulsification characteristics of a nonionic surfactant. In general, surfactants with lower HLB values are more lipophilic, while surfactants with higher HLB values are more hydrophilic. The HLB values of various poloxamines and poloxamers are provided by BASF Wyandotte Corp., Wyandotte, Mich.

Such surfactants are suitably employed in amounts from about 0.01 to about 10 weight percent, preferably 0.1 to 5 weight percent of the solution.

The ethoxylated glucose employed in the present solution preferably belongs to the class of compounds that are polyethylene glycol ethers of methyl glucose conforming generally to the formula:

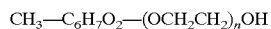

$$CH_3-C_6H_7O_2-(OCH_2CH_2)_nOH$$

(available from Amerchol Corp., Edison, N.J., as Glucam® E-10) and methyl gluceth-20 (available from Amerchol Corp., Edison, N.J., as Glucam® E-20). Such compounds are suitably employed in amounts from about 0.01 to about 5 weight percent, preferably 0.1 to 2 weight percent of the solution.

Tyloxapol is an oxyethylated tertiary octylphenol formaldehyde polymer. commercially available from a number of sources including Sanofi Winthrop, Inc. (NY, N.Y.) and Nycomed, Inc. (33 Riverside Drive, Rennselaer, N.Y. 12144). It can be prepared as disclosed in U.S. Pat. No. 2,454,541 to Bock et al. It is a known surfactant, detergent, and surface-tension reducing agent that is soluble in water. It has been used as a cleaning agent in contact lens solutions, and the present invention is directed to the combination of components with advantageous properties rather than to the use of the individual components per se.

Optionally, additional compatible surfactants that are known to be useful in contact lens wetting or rewetting solutions can be used in the solutions of this invention. The surfactant should be soluble in the lens care solution and non-irritating to eye tissues. Satisfactory non-ionic surfactants include polyethylene glycol esters of fatty acids, e.g. coconut, polysorbate, polyoxyethylene or polyoxypropylene ethers of higher alkanes ($C_{12}$–$C_{18}$). Examples include polysorbate 20 (available from ICI Americas Inc., Wilmington, Del. 19897 under the trademark Tween® 20 and Tween® 80), polyoxyethylene (23) lauryl ether (Brij® 35), polyoxyethylene (40) stearate (Myrj® 52), polyoxyethylene (25) propylene glycol stearate (Atlas® G 2612). Brij® 35, Myrj® 52 and Atlas® G 2612 are trademarks of, and are commercially available from, ICI Americas Inc., Wilmington, Del. 19897.

Various other surfactants suitable for use in the invention can be readily ascertained, in view of the foregoing description, from *McCutcheon's Detergents and Emulsifiers*, North American Edition, McCutcheon Division, MC Publishing Co., Glen Rock, N.J. 07452 and the *CTFA International Cosmetic Ingredient Handbook*, Published by The Cosmetic, Toiletry, and Fragrance Association, Washington, D.C.

In one embodiment of the invention, the solution also includes a non-ionic polymeric demulcent and viscosity builder. Such demulcents have a tendency to enhance the lens wearer's comfort by means of a film on the lens surface cushioning impact against the eye. Included among the water-soluble viscosity builders are the cellulosic polymers and derivatives thereof, for example, hydroxyethyl or hydroxypropyl methylcellulose, carboxymethyl cellulose, and cationic celluosic compounds, such as polyquaternium-10. Other polymeric demulcents include, for example, povidone, polyvinyl alcohol, and the like. Such viscosity builders may be employed in amounts ranging from about 0.01 to about 5.0 weight percent or less. Suitably, the viscosity of the final formulation is between 1 cps and 50 cps, preferably at least 2 cps. Comfort agents such as glycerin, or propylene glycol can also be added.

The preferred demulcent is hydroxypropyl methyl cellulose (HPMC). The HPMC used in the present invention suitably has a weight average molecular weight of about 5,000 to 1000,000,000. Such materials are sold by various companies, including—Dow Chemical (Midland, Mich.), for example Methocel® HPMC. In the present compositions, the HPMC is suitably present in an amount 0.01 to 10.0% by weight, preferably of between 0.05 to 5.0 percent by weight.

The present composition will contain a disinfecting amount of a preservative or an antimicrobial agent. A particularly preferred preservative is sorbic acid (0.15%). Antimicrobial agents are defined as organic chemicals that derive their antimicrobial activity through a chemical or physicochemical interaction with the microbial organisms. For example, biguanides include the free bases or salts of alexidine, chlorhexidine, hexamethylene biguanides and their polymers, and combinations of the foregoing. The salts of alexidine and chlorhexidine can be either organic or inorganic and are typically gluconates, nitrates, acetates, phosphates, sulphates, halides and the like. Preferred antimicrobial agents are the polymeric quaternary ammonium salts used in ophthalmic applications and the biguanides. More preferred are the biguanides and hexamethylene biguanides (commercially available from Zeneca, Wilmington, Del. under the trademark Cosmocil™ CQ), their polymers and water-soluble salts being most preferred. Generally, the hexamethylene biguanide polymers, also referred to as polyaminopropyl biguanide (PAPB), have molecular weights of up to about 100,000. Such compounds are known and are disclosed in U.S. Pat. No. 4,758,595 and British Patent 1,432,345, which patents are hereby incorporated herein by reference. The hydrochloride salt of polyhexamethylene biguanide is commercially available from Zeneca, Inc. under the trademark Cosmocil® CQ. This biguanide is often referred to as either "PHMB" or "PAPB," as herein, usually by the latter acronym corresponding to polyaminopropyl biguanide. Typically, biguanides are present in concentrations ranging from about 0.00001 to about 0.001% by weight.

Aqueous solution according to the present invention can be prepared by a variety of techniques. One method includes the preparation of a HPMC-containing solution by initially heating about 80 percent of the distilled water to be used, to 80° C. With agitation, the alkali metal chlorides, sequestering agents, buffering agents, surfactant, tyloxapol, and ethoxylated glucose are added. After the solution is cooled to room temperature, the sorbic acid is added, followed by the balance of distilled water. The solution can then be sterilized by forcing it through an 0.22 micron filter by means of a peristaltic pump, followed by packaging in sterilized plastic containers.

In addition to the active ingredients described above, solutions according to the present invention may contain buffers, stabilizers, isotonic agents and the like which aid in making ophthalmic compositions more comfortable to the user. The aqueous solutions of the present invention are typically adjusted with tonicity agents to approximate the osmotic pressure of normal lachrymal fluids which is equivalent to a 0.9% solution of sodium chloride or 2.5% of glycerol solution. The solutions are made substantially isotonic with physiological saline used alone or in combination, otherwise if simply blended with sterile water and made hypotonic or made hypertonic the lenses will lose their desirable optical parameters. Correspondingly, excess salt or other tonicity agent may result in the formation of a hypertonic solution that will cause stinging and eye irritation. An osmolality of about 225 to 400 mOsm/kg is preferred, more preferably 280 to 320 mOsm/kg.

The pH of the present solutions should be maintained within the range of 5.0 to 8.0, more preferably about 6.0 to 8.0, most preferably about 6.5 to 7.8. Suitable buffers may be added, such as boric acid, sodium borate, potassium citrate, citric acid, sodium bicarbonate, TRIS, and various mixed phosphate buffers (including combinations of $Na_2HPO_4$, $NaH_2PO_4$ and $KH_2PO_4$) and mixtures thereof. Borate buffers are preferred, particularly for enhancing the efficacy of PAPB. Generally, buffers will be used in amounts ranging from about 0.05 to 2.5 percent by weight, and preferably, from 0.1 to 1.5 percent.

In addition to buffering agents, in some instances it may be desirable to include sequestering agents in the present solutions in order to bind metal ions that might otherwise react with the lens and/or protein deposits and collect on the lens. Ethylene-diaminetetraacetic acid (EDTA) and its salts (disodium) are preferred examples. They are usually added in amounts ranging from about 0.01 to about 0.2 weight percent.

As indicated above, the present invention is useful for cleaning a contact lens while it is worn in the eye. Thus, as mentioned above, compositions of the present invention is especially advantageous with people who are prone to heavy lipid or like deposition or who wear lenses under an extended-wear regime. Extended wear is defined as a lens that is worn overnight, during sleep, preferably capable of wear for a week or more, even as long as one month.

The compositions of the present invention are typically sold in a wide range of small volume containers from 1 to 30 ml in size, preferably 1 ml to 20 ml in size. Such containers can be made from HDPE (high density polyethylene), LDPE (low density polyethylene), polypropylene, poly(ethylene terepthalate) and the like. Flexible bottles having conventional drop dispensing tops are especially suitable for use with the present invention.

Compositions according to the present invention may suitably be applied as follows. During wear, about one or two drops are placed directly onto each lens whenever needed. Thereafter, the wearer should blink several times.

The following specific experiments and examples demonstrate the compositions and methods of the present invention. However, it is to be understood that these examples are for illustrative purposes only and do not purport to be wholly definitive as to conditions and scope. All percentages are by weight of the solution, unless indicated otherwise.

EXAMPLE 1

An aqueous solution according to the present invention, useful as an eyedrop for contact lenses worn in the eye, can be prepared with the following ingredients in purified water:

TABLE 1

| Ingredient | gm | % w/w |
|---|---|---|
| Pluronic F127 poloxamer | 500.0 | 0.500 |
| Tyloxapol | 100.0 | 0.100 |
| Glucam ® E20 ethoxylated glucose | 100.0 | 0.100 |
| Sorbic Acid | 165.0 | 0.165 |
| Boric Acid | 677.0 | 0.677 |
| Sodium Borate | 236.0 | 0.236 |
| Sodium Phosphate (Dibasic) | 310.0 | 0.310 |
| Sodium Chloride | 155.0 | 0.155 |
| Potassium Chloride | 107.0 | 0.107 |
| HPMC (E15-LV Premium) | 200.0 | 0.200 |
| Edetate Disodium | 50.0 | 0.050 |
| Distilled Water | Q.S. 100 kg | Q.S. to 100% |

The formulation is prepared in bulk as follows. In a 316-grade stainless steel jacketed mixing vessel, hot purified water (75 to 85° C.) is added in the amount of about 95–98% of final batch volume. Under agitation the HPMC is slowly added, and agitation continued for a minimum of 20 minutes. The batch is then cooled to 20 to 25° C. with continuous agitation and then mixed for a minimum of 30 minutes. With continued agitation, the poloxamer is slowly added and mixed for a minimum of 15 minutes. Then the following batch quantities of the following ingredients are added in the order listed, wherein after one ingredient is dissolved or dispersed, the next is added: sodium chloride, potassium chloride, boric acid, sodium borate, EDTA, sodium phosphate, sorbic acid, tyloxapol, and glucam E-20 ethoxylated glucose. Agitation is maintained throughout the entire processing of the batch and the solution is mixed for a minimum of 60 minutes. Upon dissolution of these components, the batch is charged with purified water (at 20–35° C.) to the final volume. The solution is mixed for a minimum of 20 minutes to ensure complete dissolution. If necessary, the pH is adjusted to 7.0–7.20 at 25° C. with 2.5 N NaOH or 1N HCl. The osmolality is measured at 280–320 mOsm/Kg. The finished solution should be aseptically passed through a sterile 0.22 µm membrane filter.

EXAMPLE 2

This example illustrates the advantageous properties of a solution according to the present invention. In particular, 168 PureVision® contact lenses, made from balafilcon A silicone hydrogel material, were exposed to both a protein and lipid artificial deposition solution (ATS) in order to assess both the deposit inhibition of the formulation according to Example 1 ("Formulation A") compared to ReNu® Rewetting Drops which contains poloxamine, boric acid, sodium borate, sodium chloride, EDTA, and sorbic acid ("Comparative Formulation B") Comparative Formulation B consists of 0.35% sodium borate, 0.15% sorbic acid, 0.10% EDTA, 0.50% boric acid, 0.40% sodium chloride, and 0.10% poloxamine (Tetronic®) 1107.

To test for deposit inhibition, lenses were preconditioned with the Formulation A by soaking the lens in the solution for one hour prior to deposition. After deposition and incubation, the lenses were then rinsed with ReNu® Saline (no sorbic acid) and analyzed for Protein and Lipid levels respectively. The testing was conducted as follows:

A. Protocol for Testing Protein Deposit Inhibition:

In the preparation of the standards, unworn Bausch & Lomb PureVision® lenses are taken out of their vials, left to air dry and then placed in glass test tubes along with standard BSA solution. An in vitro protein mixture consisting of lysozyme, lactoferrin, human serum albumin and mucin in MOPS buffer was used. The pH of the solution is adjusted to 7.2 using 1N HCl and an osmolality equal to 326 mOsm. Seven Bausch & Lomb PureVision® lenses per test solution were preconditioned with the respective test formulations by soaking the lens in the formulation for one hour. The lenses were then removed from the formulation and placed in 1.5 mls of the Protein Mix. The lenses were then incubated in the Protein mix at 37° C. in a shaking water bath for 48 hours. Protein analysis was done using the colorimetric BCA analytical method (Sigma). The method employs the protein induced reduction of Cu(II) to Cu(I). A purple complex (Amax=562 nm) is formed following the addition of bicinchoninic acid (BCA) to the reduced copper. The intensity of the complex is shown to be directly proportional over the protein concentration range 5 µg/ml to 2000 µg/ml. Following incubation at 37° C., the rate of color development is slowed sufficiently to allow large numbers of samples to be done in a single run. The standard protein solution utilized was BSA with a standard concentration range of 0 to 50 µg. To each test tube was added 2 mls of a mixture of bicinchoninic acid (BCA) and Cu(II) Sulfate and vortexed. Tubes were then covered and placed in a water bath at 37° C. for 15 minutes. After incubation, the purple complex develops. Samples and standards are read at 562 nm in a Perkin Elmer Spectrophotometer. Protein concentration is determined from a standard plot of absorbency vs. concentration (µg). Protein results reported represent total amount of bound protein.

B. Protocol for Testing Lipid Deposit Inhibition:

Seven Bausch & Lomb PureVision® lenses per test solution were preconditioned with the respective test formulations by soaking the lens in the formulation for one hour. The lenses were then removed from the formulation, and placed in 1.5 mls of a Lipid Mix. The Lipid Mix was a mixture of palmitic acid methyl ester (PAME), cholesterol, squalene and mucin in MOPS buffer. Mucin is utilized as a surfactant to aid in the solubilization of the lipids. Lenses were then incubated in the Lipid Mix at 37° in a shaking water bath for 24 hours. After incubation, the lenses were then removed from the test solution and rinsed with ReNu® Saline (no sorbic acid) to remove any residual deposition solution. Lenses were then placed in glass vials for extraction. A three hour 1:1 CHCl$_3$/MeOH extraction was subsequently followed by a three hour Hexane extraction. Extracts were then combined and run on a Hewlett Packard GC. The column utilized was an HP-Ultra 1 with an FID detector and He as the carrier gas. Standard solutions of each of the lipids in the deposition mix were made in 1:1 CHCl$_3$/MeOH and the concentration of lipid extracted from the lenses was determined.

C. The Results:

The Percent Deposit Inhibition for protein and lipid, respectively, was calculated by the following equation:

$$\% \text{ Deposit Inhibtion} = \frac{(\text{Avg. of Control deposited lens} - \text{Avg. of Treated lens}) * 100}{\text{Avg. of Control deposited lens}}$$

where the control lens is Bausch & Lomb PureVision® balafilcon A lens deposited with the protein and lipid solution respectively.

The protein and lipid deposition values for the Bausch & Lomb PureVision® control lenses (7.75 μg and 381 μg) respectively, provided a baseline with which to assess the potential cleaning efficacy and deposit inhibition attributes of each of the formulations tested. Table 2 below represents the protein raw data and deposit inhibition results relative to the control deposited lenses. Table 2A below represents the lipid raw data and deposit inhibition results relative to the control deposited lens.

TABLE 2

Protein Deposit Inhibition and Cleaning Efficacy Data

| Test Formulation | Average Protein Deposition - Bausch & Lomb Pure Vision Control lenses | Average Protein Levels for Deposit Inhibition (μg) | % Total Protein Deposit Inhibition |
|---|---|---|---|
| Formulation A | 7.75 ug | 5.74 ug | 25.9 |
| Comparative Form. B | 7.75 ug | 6.46 ug | 16.6 |

TABLE 2A

Lipid Deposit Inhibition and Cleaning Efficacy Data and Results

| Test Formulations | Average Lipid Deposition on Pure Vision ® Control lenses | Average Lipid Levels for Deposit Inhibition (μg) | % Total Lipid Deposit Inhibition |
|---|---|---|---|
| Formulation A | 381 μg | 273 μg | 28.3 |
| Comparative Form. B | 381 μg | 321 μg | 15.7 |

As shown in Table 2A, the Formulation A appears to inhibit lipid deposition indicating that the test formulations are coating the lens in such a way as to hinder lipid uptake. With respect to protein deposit inhibition, the data in Table 2 showed that the Formulation A was the better performer, with 25.9% inhibition of protein deposition relative to the control deposited lenses with deposit inhibition of 16.6 percent.

EXAMPLE 3

The objective of this study was to evaluate the safety and tolerability of Formulation A, according to Example 1, as a rewetting drop for a continuous-wear lens compared to the currently marketed ReNu® Rewetting Drops while wearing balafilcon A (Bausch & Lomb Purevision®) tinted contact lenses for 4 hours. Twenty (20) subjects were enrolled in a 4 hour non-dispensing study comparing Formulation A to ReNu® Rewetting Drops. The subjects were all habitual soft spherical contact lens wearers. Their mean spherical Rx's were −3.25D in the test eyes and −3.00D in the control eyes. Subjects in both groups had less than 0.75D refractive cylinder. Each subject wore a pair of balafilcon A tinted contact lenses for approximately 4 hours. The eye receiving the test solution was randomly selected and remained constant for the duration of the study. Subjects were asked to place two drops of each solution into the appropriate eyes every hour until the four hour visit. The subjects and investigator were masked to solution identity. Prior to lens insertion a spherical refraction was performed through which high contrast visual acuity with high ambient illumination (HCHI) was measured. Corneal and conjunctival staining and limbal and bulbar injection were assessed with the slitlamp. Each subject was then fitted with a pair of balafilcon A tinted lenses of their power. Each lens was evaluated for centration and movement, comfort, and deposits/wettability. A spherical over-refraction was then performed. The endpoint of the over-refraction was compared to the refractive endpoint to determine the apparent "on-eye" lens power. LogMAR visual acuity under HCHI testing conditions was measured through the over-refraction. Finally, two drops of each solution were instilled into the appropriate eyes and the subject was asked to rate any sting/burn and the amount. Testing was repeated at the four hour visit in reverse order, with the exception that the baseline refraction was not repeated. Unless otherwise noted, a 2-way ANOVA incorporating Time and Solution was used to test for differences in each of the parametric dependent variables measured. Non-parametric data was analyzed by Friedman ANOVA. Differences at the $p \leq 0.05$ level were considered to be statistically significant. For Formulation A, compared to ReNu® Wetting Drops (Comparative Solution B), there were no statistically significant differences in comfort, lens movement/centration or anterior ocular physiology. A statistically significant increase in apparent lens Rx power was found for the test and control solution eyes after four (4) hours. Mean difference in apparent lens Rx was less than −0.25D, which was considered clinically insignificant. After four hours, both test and control solution eyes showed a statistically lower sting/burn visual analog score (i.e. more sting/burn). Although one subject developed nasal congestion, bulbar injection and lid margin redness after using both drops for four (4) hours (test eye was slightly worse than control eye), this reaction resolved after discontinuation of the solutions. In conclusion, Formulation A appeared to be safe and tolerable for use as an eyedrop solution.

While the invention has been described in conjunction with specific examples thereof, this is illustrative only. Accordingly, many alternatives, modifications, and variations will be apparent to those skilled in the art in light of the foregoing description and it is, therefore, intended to embrace all such alternatives, modifications, and variations as to fall within the spirit and scope of the appended claims.

What is claimed is:

1. A method of treating a contact lens in the eye with eye drops of a sterile aqueous solution comprising:
   (a) 0.01 to 1.0 percent by weight of an ethoxylated glucose derivative,
   (b) 0.01 to 1.0 percent by weight of tyloxapol,
   (c) 0.1 to 2.0 percent by weight of a polyoxyethylene-polyoxypropylene nonionic surfactant,
   (d) at least one tonicity agent which is present in an amount of 0.01 to 10.0 percent by weight; and
   (e) an effective amount of a buffering agent to maintain the pH between about 5.0 and 8.0.

2. The method of claim 1, wherein the solution further comprises a cellulose derivative in an amount of 0.01 to 5.0% by weight.

3. The method of claim 1, wherein the solution further comprises a sequestering agent which is present in an amount of 0.01 to 5.0% by weight.

4. The method of claim 1, wherein the solution is used with an extended-wear lens.

5. The method of claim 4, wherein the solution is used with a silicone hydrogel lens.

6. A system useful as an artificial tear or for rewetting or lubricating contact lenses while in the eye, said system comprising a drop dispenser capable of holding between about 1 and about 30 ml of an ophthalmic solution that comprises:
   (a) 0.01 to 1.0 percent by weight of ethoxylated glucose derivative,
   (b) 0.01 to 1.0 percent by weight of tyloxapol,
   (c) 0.1 to 2.0 percent by weight of a polyoxyethylene-polyoxypropylene nonionic surfactant,
   (d) at least one tonicity agent which is present in an amount of 0.01 to 10.0% by weight; and
   (e) an effective amount of a buffering agent.

7. A method of treating a silicone hydrogel extended-wear contact lens in the eye with eye drops of a sterile aqueous solution comprising:
   (a) 0.01 to 1.0 percent by weight of an ethoxylated glucose derivative,
   (b) 0.01 to 1.0 percent by weight of tyloxapol,
   (c) 0.1 to 2.0 percent by weight of a polyoxyethylene-polyoxypropylene nonionic surfactant,
   (d) at least one tonicity agent which is present in an amount of 0.01 to 10.0 percent by weight; and
   (e) an effective amount of a buffering agent to maintain the pH between about 5.0 and 8.0.

* * * * *